(12) United States Patent
Medoff

(10) Patent No.: US 7,749,257 B2
(45) Date of Patent: Jul. 6, 2010

(54) BEARING PLATE FOR USE IN FRACTURE FIXATION HAVING A SPHERICAL BEARING HOLE WITH YIELDING EXPANDABILITY

(75) Inventor: Robert J. Medoff, 30 Aulike St., Suite 506, Kailua, HI (US) 96734

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 771 days.

(21) Appl. No.: 11/103,923

(22) Filed: Apr. 12, 2005

(65) Prior Publication Data
US 2006/0241612 A1    Oct. 26, 2006

(51) Int. Cl.
*A61B 17/66* (2006.01)
(52) U.S. Cl. ...................................... 606/290
(58) Field of Classification Search ........... 606/61, 606/65, 66, 69, 70, 71, 73, 280, 281–299, 606/86 B
See application file for complete search history.

(56) References Cited

U.S. PATENT DOCUMENTS

| | | | | |
|---|---|---|---|---|
| 4,631,783 A | * | 12/1986 | Hayashi | 24/16 PB |
| 4,644,610 A | * | 2/1987 | Fish | 24/30.5 S |
| 5,381,588 A | * | 1/1995 | Nelson | 24/30.5 S |
| 5,578,034 A | * | 11/1996 | Estes | 606/281 |
| 6,017,345 A | * | 1/2000 | Richelsoph | 606/70 |
| 6,206,882 B1 | * | 3/2001 | Cohen | 606/283 |
| 6,235,033 B1 | * | 5/2001 | Brace et al. | 606/69 |
| 6,261,291 B1 | * | 7/2001 | Talaber et al. | 606/281 |
| 6,979,334 B2 | * | 12/2005 | Dalton | 606/61 |
| 6,989,013 B2 | * | 1/2006 | Pisharodi | 606/71 |
| 7,175,624 B2 | * | 2/2007 | Konieczynski et al. | 606/71 |
| 7,276,070 B2 | * | 10/2007 | Muckter | 606/71 |
| 2004/0167521 A1 | * | 8/2004 | De Windt | 606/69 |
| 2005/0043736 A1 | * | 2/2005 | Mathieu et al. | 606/73 |
| 2005/0096657 A1 | * | 5/2005 | Autericque et al. | 606/69 |

* cited by examiner

*Primary Examiner*—Eduardo C Robert
*Assistant Examiner*—Tara R George
(74) *Attorney, Agent, or Firm*—Ladas and Parry LLP

(57) ABSTRACT

A bearing plate for use in bone fixation for fractures, fusion osteotomies and the like, and the plate is provided with one or more spherical holes in which expandable spherical bearings can be rotatably supported. Each of the holes is formed at its periphery in such a way as to provide yielding expansibility of the hole so that upon expansion of the bearing, the hole expands with it to provide elastic resistance to the expanding bearing.

30 Claims, 5 Drawing Sheets

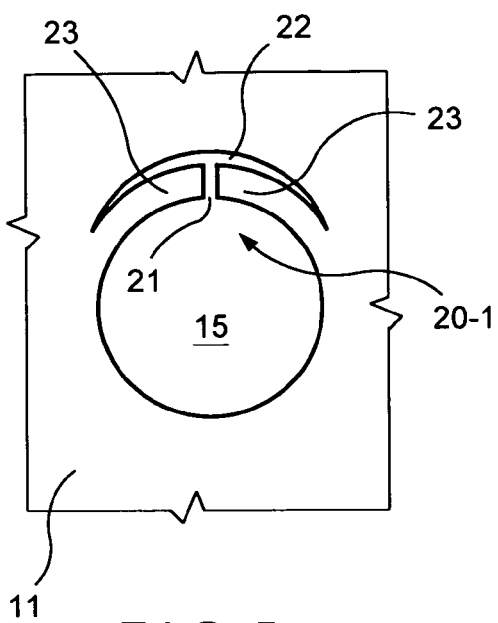
F I G. 5
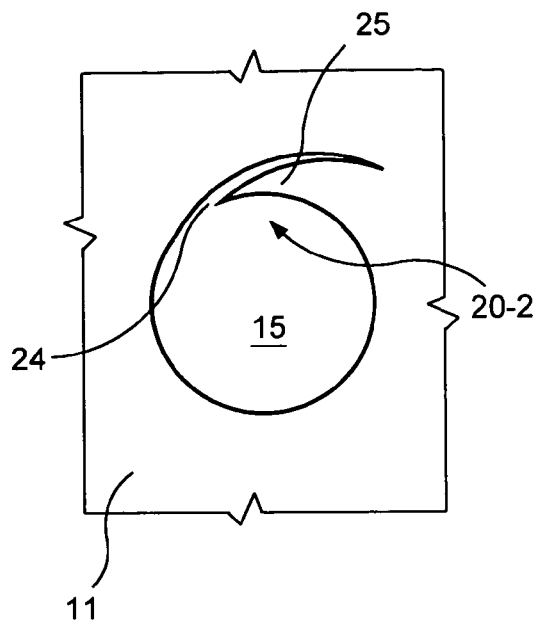
F I G. 6
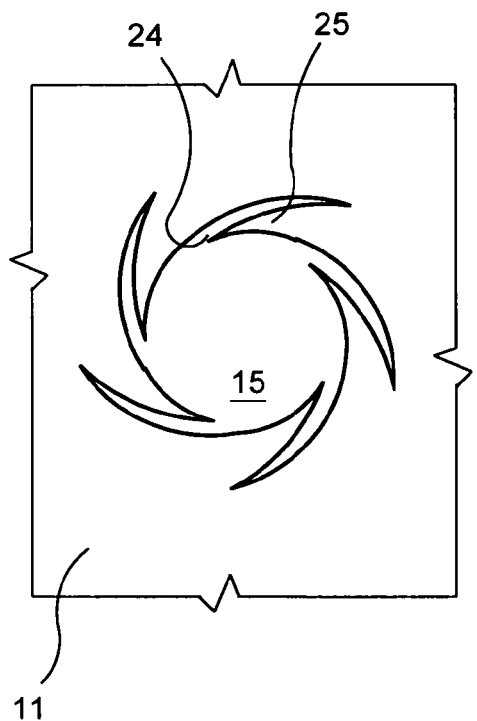
F I G. 7
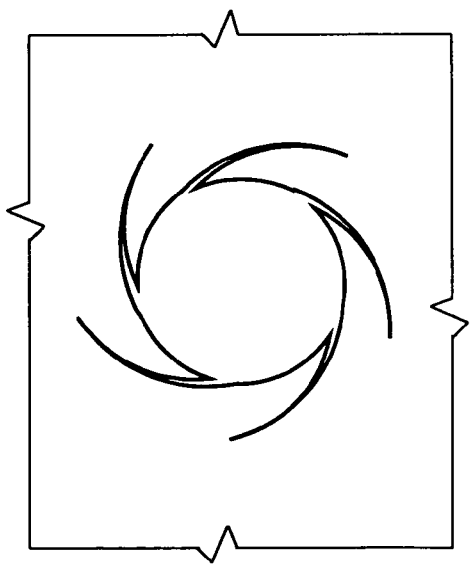
F I G. 8

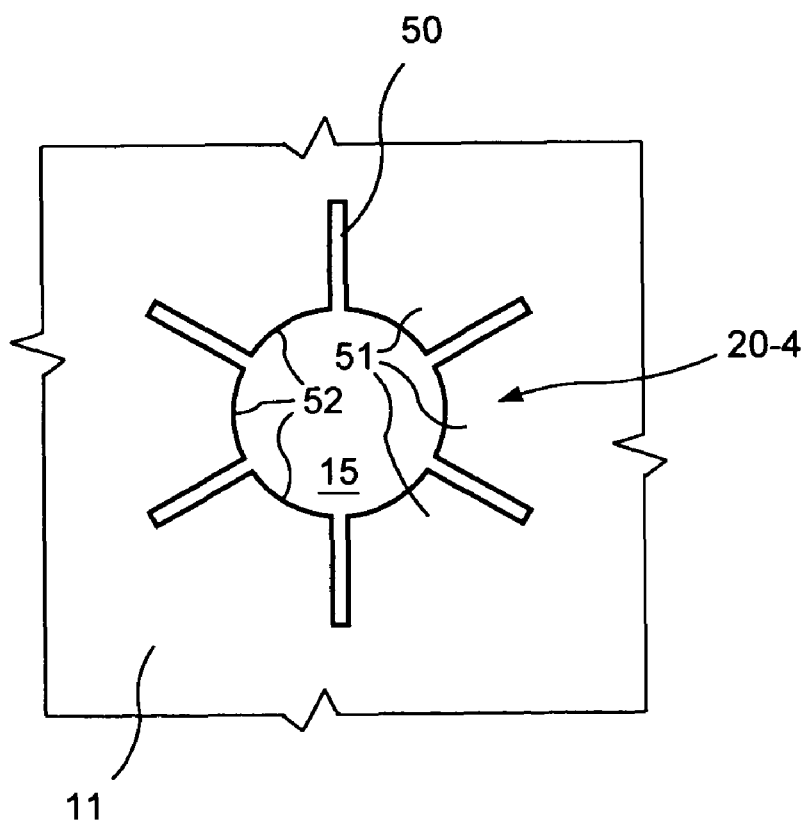
F I G. 12
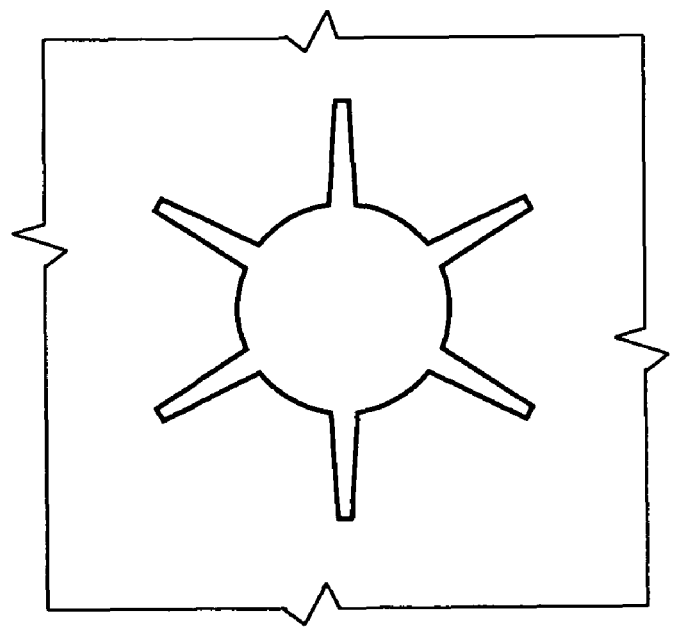
F I G. 13

BEARING PLATE FOR USE IN FRACTURE FIXATION HAVING A SPHERICAL BEARING HOLE WITH YIELDING EXPANDABILITY

FIELD OF THE INVENTION

The invention relates to a bearing plate adapted for use in fracture fixation, wherein the bearing plate has a spherical bearing hole adapted for receiving an expandable spherical bearing.

More particularly, the invention relates to improvements in the development of the bearing hole in the bearing plate.

The invention further relates to a method of moderating expansion force of an expandable spherical bearing in a bearing plate.

BACKGROUND AND PRIOR ART

The use of spherical expandable bearings in spherical holes of bearing plates is widespread. In a particular use, the bearing plate serves as a fracture fixation plate adapted for being secured at one end to a bone fragment on one side of a bone fracture and a post is inserted through the bearing into another bone fragment on an opposite side of the fracture to stabilize it. The post also serves as a means to expand the bearing and lock it in place in an adjusted angular position in the hole in the plate. Reference is made to co-pending U.S. patent application Ser. No. 10/754,462 now U.S. Pat. No. 7,195,633 which discloses such an arrangement.

It has been found that with a standard spherical hole in the bearing plate, the wall of the hole is stiff and unyielding. Consequently, as the bearing expands, initially the bearing takes up a clearance with the wall of the hole and there is no contact with the wall. Hence, there is no reactive force to fix the bearing in the hole. As soon as contact with the hole is made by the expanding bearing, the reactive forces increase substantially instantaneously with no significant yielding of the wall of the hole. Because the hole is so stiff and unyielding, the bearing cannot be expanded any further.

In the event that microgrooves are provided on the surface of the bearing, these may become deformed and if the outer diameter of the bearing diminishes by even a small amount as the edges of the microgrooves are deformed, significant loss of wall reactive force may occur.

SUMMARY OF THE INVENTION

An object of the invention is to overcome the problems associated with the rigidity and stiffness of the hole in the plate which produce instantaneous resistance and unyielding property of the hole.

further object of the invention is to obtain moderated expansion of the bearing in the hole.

A further object of the invention is to provide an elastic expansion of the hole resulting in a substantially linear production of reactive force on the wall of the hole. This has the advantage that small changes in the bearing outer diameter as it expands do not produce such drastic changes in wall reactive force. In this respect, a further object of the invention is to provide a substantially lower modulus of elasticity of the plate at the hole as compared to the modulus of elasticity of the wall for a conventional hole.

In accordance with the above and further objects of the invention, the bearing plate is provided with means at the spherical hole for providing yielding expansability at the hole so that as the bearing is expanded, the hole expands therewith to provide an elastic resistance to the expanding bearing.

In further accordance with the invention, the means which provides the yielding expansability of the hole is obtained by forming one or more elastic segments which surround the hole and are capable of deforming outwardly as the bearing expands.

In further accordance with the invention, the one or more segments can be formed by at least one slot extending outwardly from the hole.

In a particular embodiment, a radial slot extends from the hole and is joined to a circumferential slot to define two elastic segments capable of limited outward elastic deformation.

According to another embodiment, one or more slots are formed in the plate and extend outwardly and obliquely, for example circumferentially from the hole to form one or more elastic segments capable of deforming outwardly as the bearing expands.

In further accordance with the invention, the slots which are formed in the plate are configured so that the elastic resistance which is produced at the hole is proportional to expansion of the bearing.

In accordance with a further embodiment, the expandability of the hole is provided by forming a plurality of ridges at the surface of the hole which project inwardly to confront the outer surface of the bearing and be individually deformed as the bearing expands.

In further accordance with the invention, improvements are provided in a fracture fixation system in which the bearing plate is secured at one end to a bone fragment at one side of a bone fracture and at an opposite side of the bone fracture the bearing plate has an expandable spherical bearing supported in a spherical hole in the plate and wherein the bearing receives a post which is inserted into another bone fragment on an opposite side of the fracture to stabilize it, the bearing plate being provided with means at the hole to provide resilient resistance to expansion of the bearing as the bearing is being locked into secured position in an adjusted angular position in the bearing plate.

According to a further aspect of the invention, a method is provided for moderating expansion force of the expanding spherical bearing in the hole of the bearing plate as the bearing is being expanded.

In accordance with the method, one or more slots are formed in the bearing plate and are configured to define one or more resilient segments facing the bearing and which deflect outwardly when the bearing is expanded to ease resistance of the plate at the hole to the expansion of the bearing.

BRIEF DESCRIPTION OF THE DRAWINGS

FIG. 5 diagrammatically illustrates a first embodiment of means at the hole in the bearing plate for providing elastic expansion of the hole.

FIG. 6 diagrammatically illustrates a second embodiment.

FIG. 7 diagrammatically illustrates a third embodiment.

FIG. 8 shows the embodiment of FIG. 7 after expansion of the hole.

FIG. 12 diagrammatically illustrates a fifth embodiment.

FIG. 13 shows the embodiment of FIG. 12 after expansion of the hole.

DETAILED DESCRIPTION OF THE INVENTION

The invention is broadly concerned with the yieldability of a hole in a plate in which an expandable bearing is supported and expanded.

Hereafter will be described, as an example, a fracture fixation system which represents one possible, but not exclusive, use of the invention.

Figure 1:
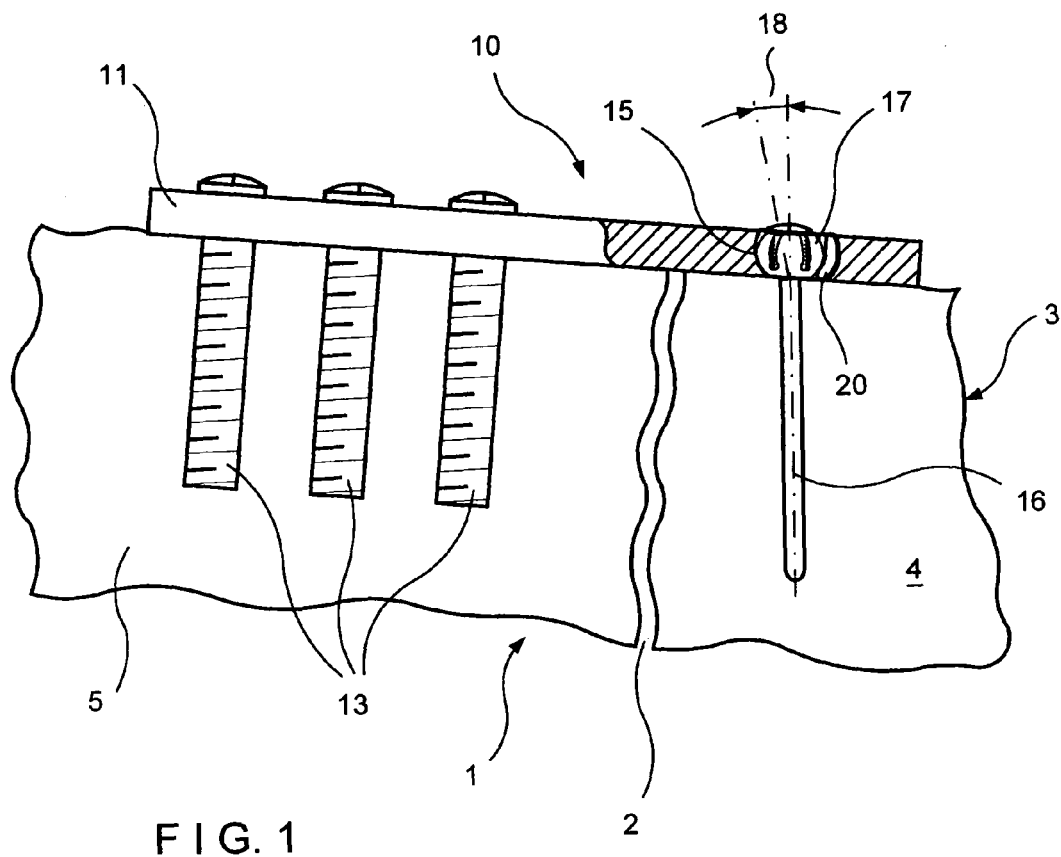
FIG. 1 is a diagrammatic sectional view illustrating a fracture fixation system including means according to the invention.
Figure 2:
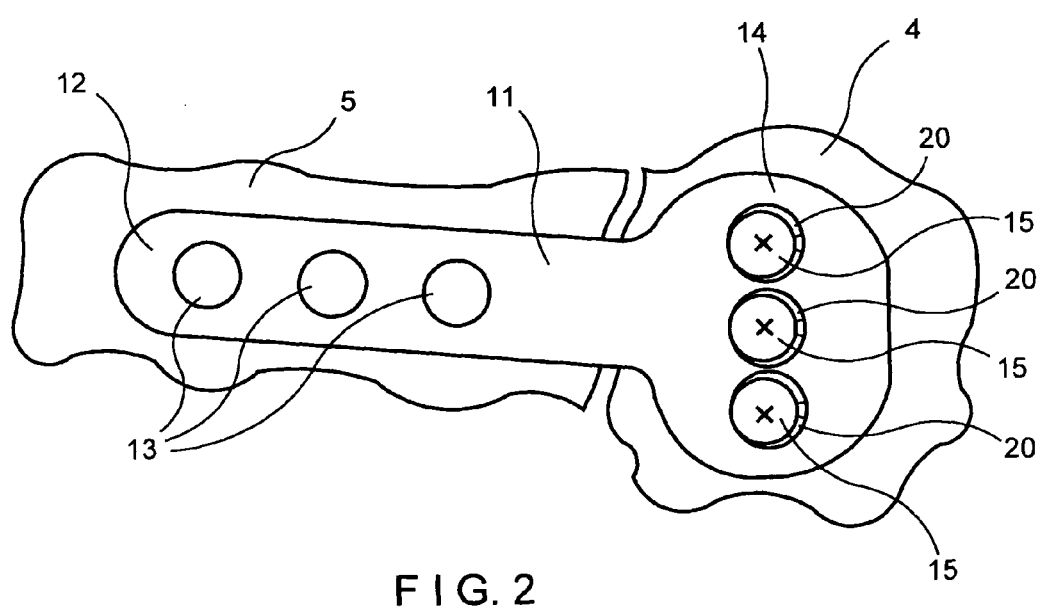
FIG. 2 is a top view thereof.

Referring to FIGS. 1 and 2, therein is shown on enlarged scale, the distal end portion of radius 1 of the wrist in which a fracture 2 is formed near the distal end 3. The fracture 2 defines an unstable distal bone fragment 4 and a stable proximal bone fragment 5.

Fixation of the fracture 2 is achieved with a fracture fixation system 10 which includes a bearing plate 11 having a proximal portion 12 fixed to the stable bone fragment 5 by bone screws 13. The bone screws 13 may have smooth heads or threaded heads that lock into a threaded hole in the bearing plate. The term "screw" is used to refer to either type of fixation.

The bearing plate 11 has a distal portion 14 with a number of spherical holes 15 in which are secured fasteners 16 which enter and are secured in the distal unstable bone fragment 4. The fasteners 16 can be in the form of pins, rods, wires, or screws, and hereafter will be referred to as posts. The posts 16 are secured in bearings 17, which are adjustably secured in the holes 15 in the bearing plate to enable the posts to be positioned at different angles 18 in the unstable fragment 4.

The bearing is formed with one or more longitudinal slits (not shown) which enable expansion of the bearing in the hole 15 when the post is advanced in an axial bore in the bearing. Expansion of the bearing by advancement of the post axially therein is well known in the art and does not form any part of the present invention and therefore is not described in any detail herein. The post is normally screwed into the bone fragment and in order to hold the bearing in the hole as the post is screwed into the bone fragment, a key and keyway connection can be provided between the bearing and the plate.

The hole 15 has a predominantly spherical shape corresponding to that of the bearing and a clearance is provided between the bearing and the hole to allow the bearing to be angularly adjusted so that the post can be inserted at a proper angle into the bone fragment 4. When the proper angle has been set, the post is axially advanced and expands the bearing to take up the clearance and thereafter press the bearing against the wall of the hole in the bearing plate to lock the bearing in the hole in the selected angular position.

Figure 3:
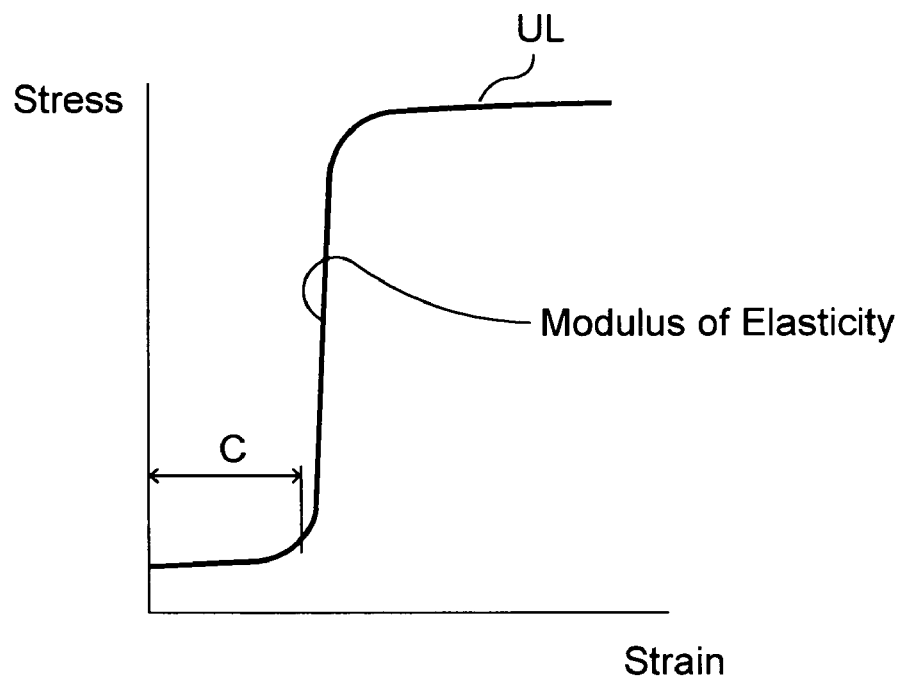
FIG. 3 shows a stress-strain diagram when a conventional spherical bearing expands in a hole in a bearing plate of the fracture fixation system.

FIG. 3 shows a stress-strain diagram for an expanding bearing in a hole in a conventional plate. As seen, the bearing, as it expands, takes up the clearance C after which the bearing presses against the wall of the hole and the force developed by the bearing against the plate rises rapidly until it reaches its ultimate limit UL. The slope of the stress-strain curve, referred to as the modulus of elasticity, is almost vertical as the wall of the hole offers little capability of expansion under the force of the expanding bearing.

In accordance with the invention, means 20 is provided at the hole 15 for providing yielding expansability at the hole so that as the bearing is expanded, the hole expands therewith to provide elastic resistance to the expanding bearing. This is a key feature of the invention and it is emphasized that it is applicable to all uses of expanding bearings in holes in plates and not only to the particular embodiment of the fracture fixation system described herein. Thus, it can be used for example, in plates employed in spine fixation which can have holes with bearings therein distributed over the area of the plate.

Figure 4:
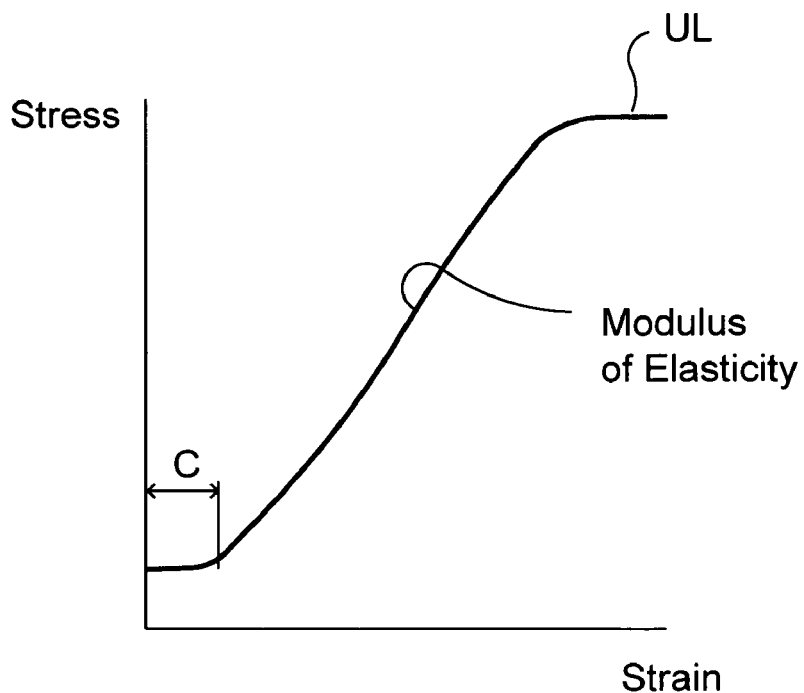
FIG. 4 shows a stress-strain diagram of the construction according to the invention.

Referring to FIG. 4, the stress-strain diagram for the expansion of the hole provided with means 20 shows that after initially taking up the clearance C between the bearing and the wall of the hole, the stress developed between the bearing and the plate rises along a much less steep modulus of elasticity before reaching the fully-developed ultimate bearing pressure UL between the expanded bearing and the wall of the hole.

FIG. 5 shows a first embodiment 20-1 of the means for providing yielding expansability of the hole 15 when the bearing is expanded. In FIG. 5 which shows a portion of the plate 11 at one of the holes 15, it is seen that a radial slot 21 is formed in the plate extending outwardly from the hole 15. The radial slot 21 extends into and is joined with a circumferential slot 22 to form segments 23 which act as elastic leaf springs. Accordingly, when the bearing is expanded, the segments 23 are capable of expanding with the expanding bearing to provide elastic resistance to the expansion of the bearing. This is evident by the reduction of the modulus of elasticity in the stress-strain diagram as shown in FIG. 4. By adjusting the size of the slots 21 and 22, the segments 23 can be provided with a defined elasticity to control the resistance to the expansion of the bearing within the hole 15. As the bearing expands and the segments 23 are outwardly deformed, the segments compress the slot 22 until they reach the outer wall of slots 22 and the bearing now is fully secured in the hole 15 at the maximum stress UL. The ends of the slots 22 may be provided with enlarged stress relief holes (not shown) to avoid crack propagation at the ends of the slots.

FIG. 6 shows a second embodiment 20-2 in which a slot 24 is provided which extends outwardly from the hole 15 in a radial direction and then obliquely in a circumferential direction to provide a flexible segment 25 which is capable of deflecting outwardly under the pressure of the expanding bearing to compress the slot 24 and eventually contact the outer wall of slot 24 when the bearing is expanded to reach the stress level UL. The slot 24 gradually decreases from the hole 15 to its remote end.

FIG. 7 is a modification of FIG. 6 in which a plurality of slots 24 are distributed uniformly around the circumference of the hole 15 to form respective segments 25 which overlie one another. The principle of operation is the same as that in FIG. 6 except that since the segments 25 extend all around the hole 15, they provide a uniformity for the resistance around the hole 15 for the expansion of the bearing. In this respect, FIG. 8 shows the segments 25 after they have been fully deflected by the expanded bearing and have compressed the slots 24.

Figure 9:
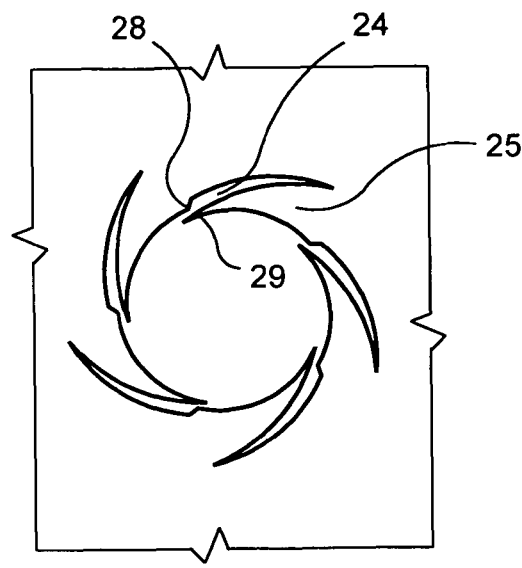
FIG. 9 shows a modification of the third embodiment.
Figure 10:
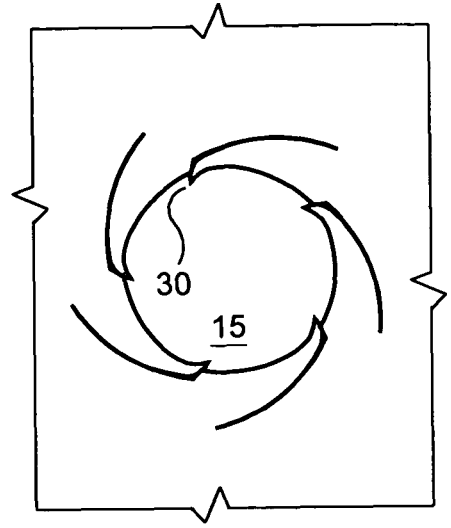
FIG. 10 shows the modification of FIG. 9 after expansion of the hole.

FIG. 9 shows a modification of the embodiment in FIG. 7, and instead of having a uniformly graduated slot 24 as shown in FIG. 7, the hole is formed with a step 28 facing the tip 29 of each segment 25. In this way, when the bearing is expanded, the tip 29 of each segment 25 bears against a respective step 28 and, as shown in FIG. 10, causes the tip 29 to be inwardly displaced in facing relation to the expanding bearing. The tip 29 is formed with a sharp pointed end 30 which serves as a tooth for biting into the outer periphery of the bearing when the bearing is expanded thereby to increase locking of the bearing in the hole.

Figure 11:
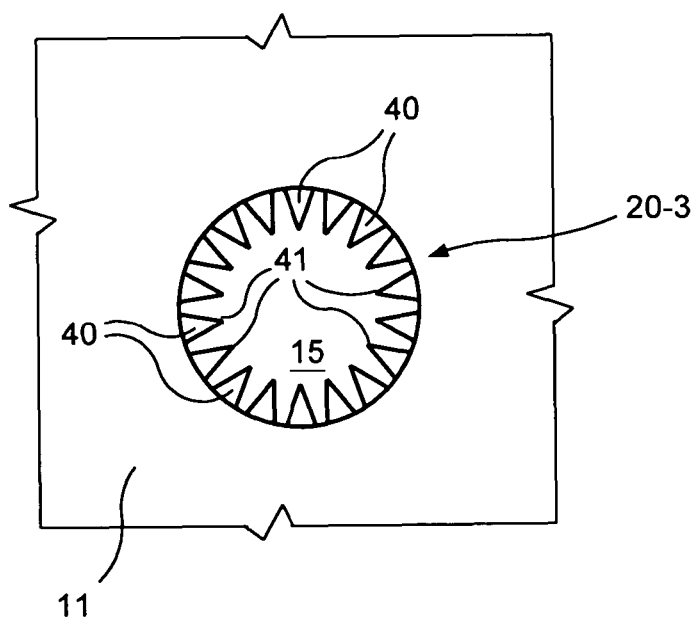
FIG. 11 diagrammatically illustrates a fourth embodiment.

FIG. 11 shows another embodiment 20-3 of the means for providing yielding expansibility at the hole in which a series of inwardly projecting ridges 40 are provided equally around the wall of the hole, the ridges extending along the thickness of the plate. The number of ridges 40 and the length thereof along the thickness of the plate is a function of the elasticity to be provided at the hole to the expandability of the bearing. In this regard, as the bearing expands, it contacts the free inner ends of the ridges 40, causing deformation of the ridges which results in a controlled elastic resistance to the expansion of the bearing and thereby achieve a stress-strain relation as shown in the stress-strain diagram of FIG. 4. As shown, the ridges 40 have pointed tips 41 to facilitate deformation of the ridges under the expansion pressure of the bearing.

FIG. 12 shows a further embodiment 20-4 of the means for providing yielding expansibility of the hole, wherein a plurality of radial slots 50 are provided around the periphery of the hole 15 so that individual segments 51 are formed between adjacent slots. As shown in FIG. 13, under the pressure of the expanding bearing, the inner surfaces 52 of the segments 51 are deformed, causing the slots to widen. Hence, the provision of the slots 50 enables the segments 51 to provide an elastic resistance to the expansion of the bearing so that the relationship between the stress produced between the bearing and the surfaces 52 with respect to the compression deformation of the surfaces 52 will conform to the stress-strain diagram of FIG. 4.

It should also be noted that while the bearings 17 have been shown as being located at the distal end of the bearing plate 11 to receive posts 16, bearings could also be located at the proximal end of the plate 11 to receive bone screws 13 or other fasteners. The invention is broadly concerned with the installation of a fastener such as a pin, rod, wire, screw or the like in an expandible predominantly spherical bearing in a corresponding predominantly spherical hole.

By way of example, a plate can be provided with one or more expandable bearings at both ends of the plate, either alone or in combination with locked or unlocked screws as particularly applicable for fixation of spinal vertebrae, osteotomies and bone fusions.

I claim:

1. A bearing plate for use in bone fixation, said plate comprising a predominately spherical hole in which an expandable spherical bearing can be rotatably supported for angulated movement through different angles and thereafter expanded to become locked a specific angle in said hole, said spherical hole having a wall facing said bearing and against which the bearing is pressed when the bearing is expanded, and means extending into said plate at said spherical hole for providing yielding expansability of the wall of said hole so that as said bearing is expanded, the spherical wall of said hole yieldingly and progressively expands therewith to provide increasing elastic resistance to the expanding bearing and deformation of the wall so that the expanded bearing becomes locked in the expanded spherical hole at said selected angle, wherein said means at said hole comprises a slot in said plate extending outwardly and obliquely from said hole, said slot being configured to be reduced in size as said hole expands to form an elastic segment capable of deforming outwardly as said bearing expands and wherein said slot forms a pointed end on said elastic segment adapted for biting into the bearing as it expands.

2. The bearing plate as claimed in claim 1, wherein said slot being configured to be reduced in size as said hole expands to form an elastic segment capable of deforming outwardly as said bearing expands.

3. The bearing plate as claimed in claim 1, wherein a plurality of said slots are arranged around said hole to form a plurality of said elastic segments which overlie one another and deflect outwardly towards one another as said hole is expanded.

4. The bearing plate as claimed in claim 3, wherein said slots are formed to provide steps on said segments which face a tip end of an adjacent segment such that as said bearing expands, said segments are deformed and cause said steps thereon to press the tip ends inwardly to bite into the expanded bearing.

5. The bearing plate as claimed in claim 1, wherein as said bearing expands in said hole, said plate offers elastic resistance which is proportional to expansion of the bearing.

6. The bearing plate as claimed in claim 1, wherein a plurality of slots are distributed around said hole defining a plurality of segments between said slots which individually deflect outwardly when the bearing expands.

7. The bearing plate as claimed in claim 1, wherein said slot is confined within said plate.

8. The bearing plate as claimed in claim 7, wherein said slot is constructed and arranged to reduce the modulus of elasticity of the plate at the hole with respect to a radial force applied by the expanding bearing.

9. The bearing plate as claimed in claim 1, wherein said spherical hole in the plate is sized to receive the spherical bearing with clearance and upon radial expansion of the bearing, first the clearance is taken up and thereafter the hole elastically yields until the bearing is fully expanded and locked in the expanded hole.

10. The bearing plate as claimed in claim 1, in combination with the spherical bearing which is radially expandable in said spherical hole in said bearing plate and wherein radial expansion of the bearing produces yielding progressive expansion of the hole and locking of the bearing in the plate.

11. In a bone fixation system having:
a post adapted for being secured to a bone segment, and
a bearing for securing the post in an adjusted angular position in a hole in a fixation plate which is adapted for being secured to another bone segment,
said bearing having an outer surface defining a predominately spherical shape adapted to rotate in said hole in the plate which has a predominately corresponding spherical shape, said bearing having a bore in which the post can extend, said bearing being radially expandable when the post is axially advanced in the bore in the bearing,
the improvement comprising:
one or more slots in said plate extending outwardly from said hole and confined in the plate, to define resilient segments which individually deflect outwardly upon expansion of said bearing to provide resilient resistance to expansion of the bearing, said resilient segments being arranged to be deflected by the expanded bearing to narrow said one or more slots and produce increasing pressure against the expanding bearing to lock the bearing in the hole wherein said resilient segments overlie one another and upon expansion of said bearing each resilient segment deflects outwardly towards an adjacent resilient segment to narrow the slot therebetween to lock the expanded bearing in the hole.

12. The improvement as claimed in claim 11, wherein said resilient segments form leaf springs overlying one another separated by said slots.

13. The improvement as claimed in claim 11, wherein said one or more slots are curved.

14. The improvement as claimed in claim 11, wherein said one or more slots extend radially and obliquely in said plate from said hole.

15. The improvement as claimed in claim 11, wherein at least some of said resilient segments have pointed inner ends forming teeth for biting into said bearing during expansion of the bearing.

16. The improvement as claimed in claim 11, wherein said bearing and said hole include a key and keyway connection to prevent rotation of the bearing in the hole as the post is advanced in the bore in the bearing.

17. The improvement as claimed in claim 11, wherein a plurality of slots are uniformly distributed around said hole.

18. The improvement as claimed in claim 11, wherein the bone fixation system is adapted for fracture fixation wherein the post is adapted to be secured to a bone fragment on one side of a bone fracture and the fixation plate is adapted to be secured to a stable bone.

19. A method of moderating expansion force of an expandable spherical bearing in a bone fixation plate adapted to be secured to a bone segment when a bone fixation element is advanced in the expandable bearing, said method comprising the steps of:

providing a spherical hole in said plate in which the spherical bearing is initially rotatably supported and adapted for angulated movement about an axis of the hole, providing at least one slot in the plate extending outwardly from a said spherical hole in the plate in which the spherical bearing is rotatably supported, axially advancing a bone fixation element in the bearing in a angularly adjusted position of the bearing to progressively secure the bone fixation element in the bone segment at a determined angle while concurrently expanding the bearing, and arranging said at least one slot to define one or more resilient segments facing the bearing thereby causing said segments to deflect outwardly when the bearing expands to ease resistance of the plate to the expansion of the bearing until the bearing becomes locked in the expanded spherical hole in a selected angulated position in the bone wherein the expansion of said bearing causes said one or more resilient segments to narrow said at least one slot as the resilient segments are deflected by the expanding bearing.

20. The method as claimed in claim 19, comprising forming steps on said segments to press tips of adjacent segments inwardly, to bite into the bearing, as the hole is expanded.

21. The method as claimed in claim 20, comprising forming said tips with pointed ends.

22. The method as claimed in claim 19, adapted for fracture fixation comprising securing the fixation plate to the bone segment on one side of a bone fracture and securing the bone fixation element into another bone segment on an opposite side of the bone fracture.

23. A bone fixation system comprising:

a post adapted for being secured to a bone segment, and a fixation plate having a spherical hole therein a bearing for securing the post in an adjusted angular position in said spherical hole in said fixation plate which is adapted for being secured to another bone segment, said bearing having an outer surface defining a predominately spherical shape adapted to initially rotate in said hole in the plate to adjust angularity of the post, said hole having a predominately spherical shape corresponding to the shape of said bearing, said bearing having a bore in which the post can extend, said bearing being radially expandable when the post is axially advanced in the bore in the bearing, said plate having one or more slots extending outwardly from said hole to define resilient segments which deflect outwardly of the hole upon radial expansion of said bearing to provide resilient resistance of the hole to the radial expansion of the bearing and locking of the expanded bearing in the expanded hole wherein said resilient segments overlie one another and upon expansion of said bearing each resilient segment deflects outwardly towards an adjacent resilient segment to narrow the slot therebetween.

24. The bone fixation system as claimed in claim 23, wherein said resilient segments form overlying leaf springs separated by said slots.

25. The bone fixation system as claimed in claim 23, wherein said slots are curved outwardly in said plate from said hole.

26. The bone fixation system as claimed in claim 23, wherein said slots extend within said plate radially and obliquely from said hole.

27. The bone fixation system as claimed in claim 23, wherein at least some of said resilient segments have pointed inner ends forming teeth for biting into said bearing during radial expansion of the bearing.

28. The bone fixation system as claimed in claim 23, wherein said bearing and said plate include a key and keyway connection to prevent rotation of the bearing in the hole as the post is advanced in the bore in the bearing.

29. The bone fixation system as claimed in claim 23, wherein said plurality of slots are uniformly distributed around said hole.

30. The bone fixation system as claimed in claim 23, wherein the post is adapted to be secured to the bone segment on one side of a bone fracture and the fixation plate is adapted to be secured to said another bone segment on an opposite side of the bone fracture.

* * * * *